United States Patent [19]

Schiehser et al.

[11] Patent Number: 4,622,402

[45] Date of Patent: * Nov. 11, 1986

[54] PROCESS FOR PREPARING THIENO-FUSED HETEROCYCLIC ANTI-ULCER AGENTS AND INTERMEDIATES THEREFOR

[75] Inventors: Guy A. Schiehser, Malvern; Donald P. Strike, St. Davids, both of Pa.

[73] Assignee: American Home Products Corporation, New York, N.Y.

[*] Notice: The portion of the term of this patent subsequent to Dec. 25, 2001 has been disclaimed.

[21] Appl. No.: 767,558

[22] Filed: Aug. 20, 1985

Related U.S. Application Data

[63] Continuation-in-part of Ser. No. 655,980, Sep. 28, 1984.

[51] Int. Cl.[4] ........................................... C07D 275/00
[52] U.S. Cl. .................................................... 548/212
[58] Field of Search ................................ 548/211, 212

[56] References Cited

U.S. PATENT DOCUMENTS 4,490,527 12/1984 Schiehser et al. ................... 548/212

FOREIGN PATENT DOCUMENTS 2111988 12/1983 United Kingdom ................ 548/211

OTHER PUBLICATIONS

Noller, Carl, *Textbook of Organic Chemistry*, W. B. Saunders, Philadelphia (1966) p. 263.

*Primary Examiner*—Glenna M. Hendricks
*Attorney, Agent, or Firm*—George Tarnowski

[57] ABSTRACT

A process for preparing certain thieno-fused heterocyclic compounds having $H_2$-receptor antagonist and antisecretory activity, which involves the reaction of a mercaptan, obtained by reduction of a thienoisothiazole amino alkyl disulfide, with a 5-substituted-2-furanylmethanol; and said thienoisothiazole amino alkyl disulfide intermediates.

2 Claims, No Drawings

PROCESS FOR PREPARING THIENO-FUSED HETEROCYCLIC ANTI-ULCER AGENTS AND INTERMEDIATES THEREFOR

This is a continuation-in-part of U.S. Ser. No. 655,980, filed Sept. 28, 1984.

This invention relates to a novel process for the preparation of certain thieno-fused heterocyclic compounds and intermediates useful in the process. The products are disclosed in U.S. Pat. No. 4,490,527. The process of the present invention gives the products in good overall yield from conveniently available starting materials.

The present invention provides a process for the preparation of thienofused heterocyclic compounds of the formula

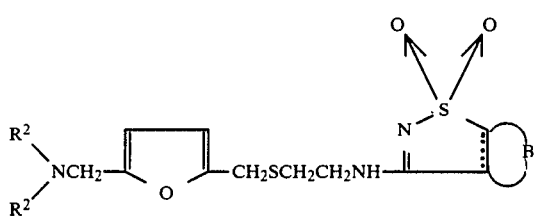

wherein B is a moiety having the formula

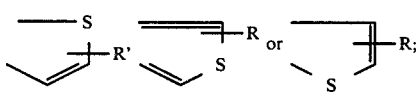

R is hydrogen, mono- or dihalo, nitro, cyano, trifluoromethyl, lower alkyl, lower alkoxy, lowercycloalkyl, mono-or di-lower alkyl substituted amino, alkanoylamino, lower alkyl thio, loweralkylsulfonyl, sulfamoyl, lower alkyl substituted sulfamoyl, phenyl or phenyl substituted with halo, lower alkyl, lower alkoxy, trifluoromethyl, cyano or nitro; $R^1$ and $R^2$ are each lower alkyl or $R^1$ and $R^2$ taken together, optionally with a hetero atom, form a saturated 5- or 6-membered heterocyclic ring; and the pharmacologically acceptable salts thereof, and intermediates which are used in said process.

The process comprises (A) reducing a disulfide having the formula

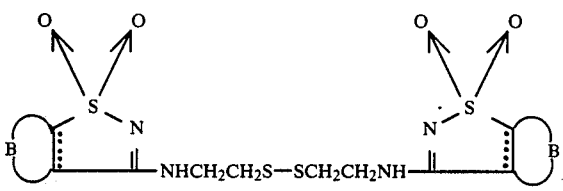

wherein B is as defined hereinbefore; and (B) reacting the intermediate obtained in Step A with a compound of the formula

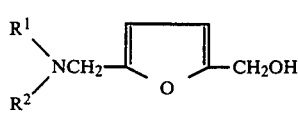

wherein $R^1$ and $R^2$ are as defined hereinbefore to yield a compound having the formula

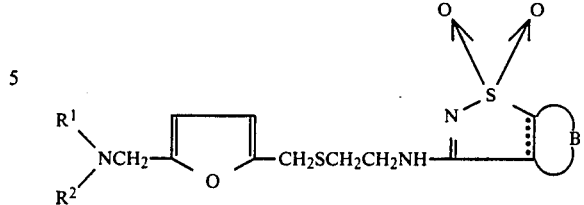

wherein B, $R^1$ and $R^2$ are as defined hereinbefore, and if desired, converting a resulting free base into a pharmacologically acceptable salt.

The term "halo" refers to fluoro, chloro and bromo. The terms "loweralkyl" and "loweralkoxy" refer to moieties having 1 to 6 carbon atoms in the carbon chain. The term "lower cycloalkyl" refers to cyclic structures having 5 to 7 carbon atoms. The term "alkanoyl" refers to the moiety RCO-wherein R is an alkyl group having 1 to 4 carbon atoms.

The reduction of the disulfide of formula

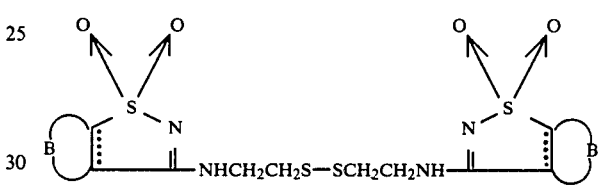

is carried out in an organic solvent, for example methanol, using a reducing agent, preferably excess sodium borohydride. The resulting mercaptan is recovered from the reaction mixture by conventional procedures and is reacted in its unisolated form in the subsequent step with the furanylmethanol derivative of formula

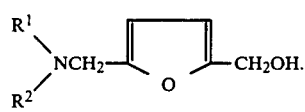

The latter reaction is carried out by adding, with cooling, the mercaptan mixture to the furanylmethanol derivative and then storing the resulting mixture at reduced temperature, for example about 5° C. Recovery of the product is by conventional techniques, and the final product is likewise purified by conventional techniques, as for example preparative layer chromatography.

The final products obtained in their free base form can be converted into pharmacologically acceptable salts by standard procedures. For example, the free base can be dissolved in a suitable organic solvent and the solution treated with a solution of the selected acid, in accordance with conventional procedures for preparing pharmacologically acceptable salts. As examples of suitable acids, there may be used hydrochloric, hydrobromic, sulfuric, nitric, phosphoric, acetic, maleic, fumaric, citric, methanesulfonic, p-toluenesulfonic and the like.

The disulfide intermediate used in the present process can be prepared in several ways. In one method, the following reaction sequence is involved

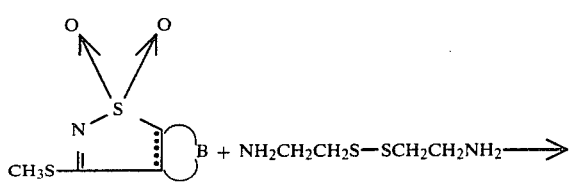

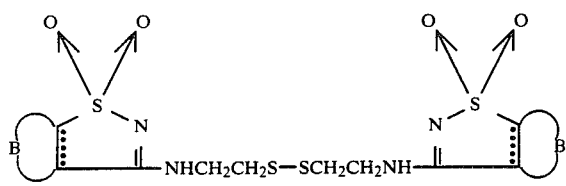

The starting compound 3-(methylthio)thieno[3,4-d]isothiazole 1,1-dioxide, in turn, can be prepared as follows:

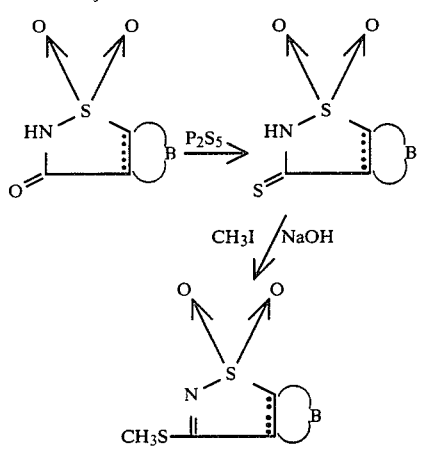

The starting compounds, for example thieno[3,4-d]isothiazol-3(2H)-one 1,1-dioxide, are available commercially or can be prepared by the procedures described by Rossy et al., *J. Org. Chem.*, 45, 617 (1980).

In another method, the disulfide intermediate can be prepared as follows:

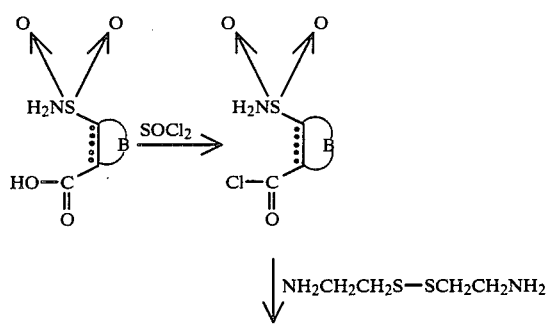

-continued

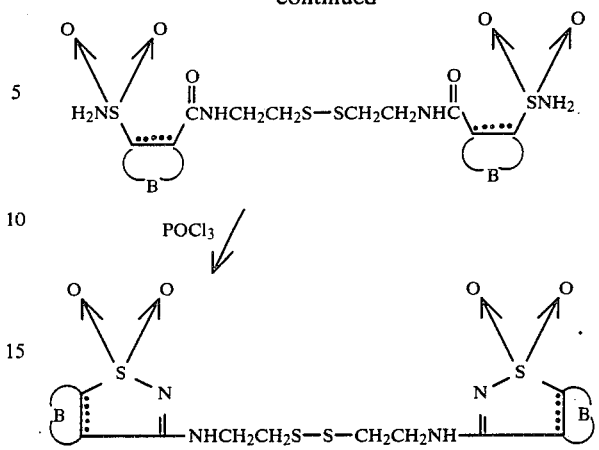

The starting intermediates having the formula $$R^1\!\!\diagdown\!\!N\text{---}CH_2\text{---}\!\!\underset{O}{\underbrace{\phantom{xxxx}}}\!\!\text{---}CH_2OH$$
$$R^2\!\!\diagup$$

can be conveniently prepared according to the following procedure described in U.S. Pat. No. 4,128,658, as for example the dimethylaminomethyl derivative:

$$\underset{O}{\underbrace{\phantom{xxxx}}}\text{---}CH_2OH \xrightarrow[\text{HCHO}]{(CH_3)_2NH}$$

$$CH_3\!\!\diagdown\!\!N\text{---}CH_2\text{---}\!\!\underset{O}{\underbrace{\phantom{xxxx}}}\!\!\text{---}CH_2OH$$
$$CH_3\!\!\diagup$$

The resulting desired intermediate can be recovered by known means and can be used directly in the process of the invention.

The process of the invention can be used to prepare compounds such as those disclosed in U.S. Ser. No. 468,221 filed Feb. 22, 1983, now U.S. Pat. No. 4,490,527 and which have been described, supra. These compounds are potent $H_2$-receptor antagonists and antisecretory agents, which are useful in the treatment of conditions where there is hypersecretion of gastric acid, such as in gastric and peptic ulceration, and other conditions caused or exacerbated by gastric acidity, such as stress ulceration or gastric intestinal bleeding due to trauma.

The following examples illustrate this invention.

PREPARATION OF 5-(DIMETHYLAMINO)METHYL-2-FURANMETHANOL

A mixture of 196 g (2 mol) of furfuryl alcohol, 245 g (3 mol) of dimethylamine hydrochloride and 200 mL of 37% formaldehyde is stirred at 0° C. for 3 hours. The mixture is allowed to warm to room temperature and is stirred for 20 hours.

The mixture is treated with 750 g of sodium carbonate and the resulting slurry is extracted sequentially with ethyl acetate and acetone. The combined organic extracts are rotoevaporated and distilled to give, in two fractions, 209 g (67.3%) of the title compound.

Fraction A b.p. 91°–96° C. [0.4 mm] 147.1 g

Analysis for: $C_8H_{13}NO_2$: Calculated: C, 61.91; H, 8.44; N, 9.03. Found: C, 61.25; H, 8.59; N, 8.86.

Fraction B b.p. 96°–98° C. [0.4 mm] 61.9 g

Analysis for: $C_8H_{13}NO_2$: Calculated: C, 61.91; H, 8.44; N, 9.03. Found: C, 61.79; H, 8.41; N, 9.19.

PREPARATION OF THE DISULFIDE INTERMEDIATE

Method A (1) 3-(Methylthio)thieno[3,4-d]isothiazole 1,1-dioxide (a) Thieno[3,4-d]isothiazol-3(2H)-thione 1,1-Dioxide To a mixture of 5.6 g. (0.03 mole) of thieno[3,4-d]isothiazol-3(2H)-one 1,1-dioxide* in 50 ml. of dry pyridine is added 5.6 g. (0.016 mole) of phosphorus pentasulfide portionwise over 3 minutes. The viscous mixture is slowly heated in an oil bath under an atmosphere of nitrogen. The temperature of the oil bath is slowly increased to 80° C. after 30 minutes. The temperature of the oil bath is then kept at 80° C. for 25 minutes, the internal temperature reading 63° C. The solution is cooled to 50° C. and is added dropwise over 5 minutes to 200 ml. of water and cooled in an ice bath. The precipitate which forms is collected and discarded. The filtrate is cooled in ice and acidified with concentrated hydrochloric acid to pH 1. The precipitate which forms is collected to yield 40% of material. In another expeirment, a sample is recrystallized from water to obtain an analytical sample, m.p. 196°–8° C. (dec.).

*Prepared according to the procedures described by Rossy et al., *J. Org. Chem.*, 45, 617 (1980).

Analysis for: $C_5H_3NO_2S_3$: Calculated: C, 29.26; H, 1.47; N, 6.82. Found: C, 29.91; H, 1.43; N, 6.87.

(b) 3-(Methylthio)thieno[3,4-d]isothiazole 1,1-dioxide

To a mixture of 0.9 g. (0.0044 mole) of thieno[3,4-d]isothiazole-3(2H)-thione 1,1-dioxide in 4 ml. of ethanol is added a solution of 0.35 g. (0.0044 mole) of 50% sodium hydroxide in 3 ml. of water. To this thick mixture is added 0.62 g. (0.0044 mole) of iodomethane. The mixture is heated under reflux for 5 minutes, and then filtered to give 0.35 g. of product. On cooling, a second crop of 0.1 g. of material is obtained. A small amount of the first crop is recrystallized from ethanol to afford an analytical sample, m.p. 184°–6° C.

Analysis for: $C_6H_5NO_2S_3$: Calculated: C, 32.86; H, 2.30; N, 6.39. Found: C, 32.76; H, 2.27; N, 6.43.

(2)

To 50 ml of ice-cold methanol is added 138 mg (6 mmol) of sodium metal. After dissolution, the solution of sodium methoxide is added with cooling to a methanol solution of 676 mg (3 mmol) of cystamine dihydrochloride. After 2 hours, the mixture is rotoevaporated and the resulting residue dissolved in absolute ethanol. 3-(Methylthio)thieno[3,4-d]isothiazole 1,1-dioxide (1.31 g, 6 mmol) of Step 1 above is added and the mixture refluxed for 1.5 hours.

Upon cooling, the mixture is filtered and dried to give crude disulfide. Trituration with water, filtration and drying affords 691 mg of the title compound, m.p. 282°–285° C.

Analysis for: $C_{14}H_{14}N_4O_4S_6$: Calculated: C, 33.99; H, 2.85; N, 11.33. Found: C, 33.59; H, 2.73; N, 10.78.

Method B (1) 4-Aminosulfonyl-3-thiophenecarbonylchloride

A solution of 1.0 g of 4-aminosulfonylthiophene-3-carboxylic acid in 20 ml of thionyl chloride is heated in an oil bath maintained at 90° C. for 2 hours. Rotoevaporation gives 1.0 g of the title compound, m.p. 236°–238° C.

Analysis for: $C_5H_4ClNO_3S_2$: Calculated: C, 26.60; H, 1.79; N, 6.21. Found: C, 26.57; H, 1.78; N, 5.92.

(2)

A solution of cystamine (generated from 1.0 g (4.4 mol) of cystamine dihydrochloride with methanolic sodium methoxide) in 10 ml of dimethylformamide is treated with 2.0 g (8.9 mmol) of the acid chloride of Step 1 above. After 2.25 hours the solvent is removed by rotoevaporation and the residue partitioned between water and ethyl acetate. The organic extract is dried over magnesium sulfate and rotoevaporated to a white solid. Crystallization from absolute ethanol gives the title compound, m.p. 210°–214° C.

Analysis for: $C_{14}H_{18}N_4O_6S_6$: Calculated: C, 31.68; H, 3.42; N, 10.36. Found: C, 32.65; H, 3.57; N, 10.87.

(3)

A suspension of 190 mg (0.36 mmol) of the sulfonamide of Step 2 above in 2 ml of phosphorus oxychloride is heated to reflux and maintained until dissolution is complete (1.5 hours).

The mixture is rotoevaporated and suspended in water to give, after filtration and drying, the title compound, m.p. 277°–281° C.

Thin layer chromatography shows the product to be identical to the product obtained by Method A, above.

EXAMPLE 1

N-[2-[[[5-[(Dimethylamino)methyl]-2-furanyl]methyl]thio]ethyl]thieno[3,4-d]isothiazol-3-amine 1,1-dioxide A suspension of 49 mg (0.1 mmol) of the disulfide prepared according to either of the methods disclosed supra is dissolved in 40 ml of methanol and treated portionwise with excess sodium borohydride. After two hours the mixture is rotoevaporated and the residue partitioned between dilute aqueous hydrochloric acid and methylene chloride. The organic extract is dried over magnesium sulfate, rotoevaporated and the residual oil dissolved in 2 ml of ice-cold concentrated hydrochloric acid. 5-[(Dimethylamino)methyl]-2-furanylmethanol (31 mg, 0.2 mmol) is added with cooling and the resulting mixture stored at 5° C. for 16 hours.

The mixture is treated with excess sodium carbonate at ice-bath temperature, extracted with methanol and rotoevaporated to give crude product. Preparative layer chromatography (silica gel; methanol) gives the title compound: m.p. 182°–186° C.

Analysis for: $C_{15}H_{19}N_3O_3S_3$: Calculated: C, 46.77; H, 4.97; N, 10.90. Found: C, 46.41; H, 4,92; N, 10.97.

What is claimed is:

1. A compound having the formula

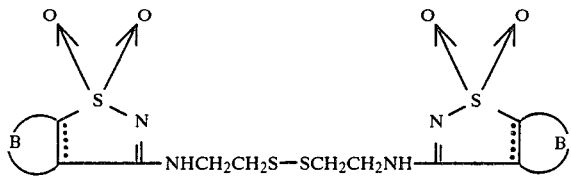

wherein B is a moiety having the formula

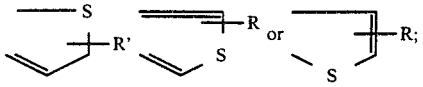

and

R is hydrogen, mono- or dihalo, nitro, cyano, trifluoromethyl, lower alkyl, lower alkoxy, lowercycloalkyl, mono-or di-lower alkyl substituted amino, alkanoylamino, lower alkyl thio, loweralkylsulfonyl, sulfamoyl, lower alkyl substituted sulfamoyl, phenyl or phenyl substituted with halo, lower alkyl, lower alkoxy, trifluoromethyl, cyano or nitro.

2. The compound of claim 1 having the name bis-[3-(ethylamino)thieno[3,4-d]isothiazole 1,1-dioxide]dithioether.

* * * * *